US 6,593,146 B1

(12) United States Patent
Lang et al.

(10) Patent No.: US 6,593,146 B1
(45) Date of Patent: Jul. 15, 2003

(54) METERING DEVICE AND METHOD FOR OPERATING A METERING DEVICE

(75) Inventors: Andreas Lang, Marktheidenfeld (DE); Hubert Kunze, Kreuzwertheim (DE); Eberhard Albrecht, Wertheim (DE); Peter Mahler, Kreuzwertheim (DE)

(73) Assignee: Brand GmbH & Co. KG Fabrik fur Laborgerate, Wertheim (DE)

( * ) Notice: Subject to any disclaimer, the term of this patent is extended or adjusted under 35 U.S.C. 154(b) by 0 days.

(21) Appl. No.: 09/673,530

(22) PCT Filed: Feb. 16, 2000

(86) PCT No.: PCT/EP00/01260

§ 371 (c)(1),
(2), (4) Date: Oct. 17, 2000

(87) PCT Pub. No.: WO00/49418

PCT Pub. Date: Aug. 24, 2000

(30) Foreign Application Priority Data

Feb. 16, 1999 (DE) ............................ 199 06 409

(51) Int. Cl.[7] ............................ G01N 1/10; G01N 1/14; G01N 1/00; G01N 1/24; B01L 3/02; B01L 3/00; B01L 9/00

(52) U.S. Cl. ........................ 436/180; 422/100; 422/102; 422/104; 73/863.25; 73/863.22; 73/863.83; 73/863.85; 73/863.86; 73/864; 73/864.01; 73/864.11; 73/864.16; 73/864.34

(58) Field of Search ................................ 422/100, 102, 422/104; 436/180; 73/863.05, 863.32, 863.81, 863.83, 863.85, 863.86, 864, 864.01, 864.02, 864.11, 864.12, 864.15, 864.16, 864.34, 864.35

(56) References Cited

U.S. PATENT DOCUMENTS

| 2,463,481 | A | * | 3/1949 | Ferraez, Jr. ............... 417/128 |
|---|---|---|---|---|
| 2,475,857 | A | * | 7/1949 | Reinert ..................... 73/863.12 |
| 2,933,376 | A | * | 4/1960 | McBrien ....................... 141/24 |
| 3,012,863 | A | * | 12/1961 | Feichtmeir ................... 422/100 |
| 3,184,122 | A | * | 5/1965 | Nerenberg ................... 222/255 |
| 3,192,969 | A | * | 7/1965 | Baruch et al. ......... 137/625.65 |
| 3,219,417 | A | * | 11/1965 | Klingbeil et al. ........... 422/100 |
| 3,273,402 | A | * | 9/1966 | Farr ............................ 137/860 |
| 3,476,518 | A | * | 11/1969 | Jungner ................. 137/625.19 |
| 3,492,876 | A | * | 2/1970 | Bull et al. ..................... 141/27 |
| 3,572,552 | A | * | 3/1971 | Guinn ......................... 222/263 |
| 3,581,575 | A | * | 6/1971 | Butler ......................... 222/135 |
| 3,632,199 | A | * | 1/1972 | Carpenter ................... 251/309 |
| 3,645,698 | A | * | 2/1972 | Holybee et al. ............. 222/365 |
| 4,011,685 | A | * | 3/1977 | Boyd et al. ................. 422/100 |
| 4,101,283 | A | * | 7/1978 | Sundstrom ................... 222/333 |
| 4,140,020 | A | * | 2/1979 | Cook ............................ 141/2 |
| 4,295,801 | A | * | 10/1981 | Bennett ....................... 417/397 |
| 4,459,267 | A | * | 7/1984 | Bunce et al. ................ 222/207 |
| 4,475,410 | A | * | 10/1984 | Jaeger ..................... 73/863.84 |
| 4,493,896 | A | * | 1/1985 | La Motte et al. ............. 422/99 |
| 4,593,728 | A | * | 6/1986 | Whitehead et al. ......... 141/234 |
| 4,780,833 | A | * | 10/1988 | Atake ......................... 422/923 |
| 5,104,621 | A | * | 4/1992 | Pfost et al. .................. 422/100 |
| 5,226,462 | A | * | 7/1993 | Carl ............................. 141/1 |
| 5,341,691 | A | * | 8/1994 | Callis et al. ............. 73/863.81 |
| 5,360,596 | A | * | 11/1994 | Pennatto ..................... 422/100 |
| 5,396,812 | A | * | 3/1995 | Peterson ................... 73/863.25 |
| 5,456,879 | A | * | 10/1995 | Suovaniemi ................ 422/100 |
| 5,525,302 | A | * | 6/1996 | Astle ......................... 422/100 |
| 6,006,800 | A | * | 12/1999 | Nakano ..................... 141/130 |
| 6,019,004 | A | * | 2/2000 | Conley et al. ............. 422/923 |
| 2001/0036425 | A1 | * | 11/2001 | Gazeau et al. ............. 422/100 |

* cited by examiner

*Primary Examiner*—Jill Warden
*Assistant Examiner*—Brian R Gordon
(74) *Attorney, Agent, or Firm*—Blackwell Sanders Peper Martin LLP

(57) ABSTRACT

A dosing device is provided and comprises a withdrawal container and a dosing means comprising at least one dosing unit which is a piston-cylinder unit designed as a disposable member. The piston-cylinder unit discharges into a receiving container and valve means is provided to control flow into and out of the piston-cylinder unit.

22 Claims, 2 Drawing Sheets

METERING DEVICE AND METHOD FOR OPERATING A METERING DEVICE

CROSS-REFERENCE TO RELATED APPLICATION

This Application claims priority of PCT application WO 00/49418 which is based on German Patent Application 199 06 409.1 filed Feb. 16, 1999.

BACKGROUND OF THE INVENTION

The present invention relates to a dosing device and to a method for operating a dosing device.

A dosing device which is used in practice, comprises at least one withdrawal container and a dosing means which is in line communication with the withdrawal container and discharges the medium to be dosed to receiving containers. Such a dosing system may e.g. be of a multi-channel type including a piston system; its technical construction is complicated and it consists of high-quality materials and is thus an expensive construction. Further problems arise from wear which is normally high. Furthermore, a change in the medium requires a troublesome cleaning process, and tests carried out with a current device have revealed that it is difficult, particularly when using media, to adequately clean and, if necessary, sterilize the pistons systems because the piston systems often comprise undercuts of complicated shapes.

SUMMARY OF THE INVENTION

It is therefore the object of the present invention to provide a dosing system of the construction of which is much more simple than those of known dosing systems and which is thus less complicated from a structural point of view and can be operated more easily.

In the inventive dosing device, the dosing means comprises at least one dosing unit which is constructed as a uniform piston-cylinder unit designed as a disposable member. This has the effect that, in contrast to known dosing devices, the piston-cylinder unit can easily and efficently be replaced, and disposed of, if necessary. The present invention permits the elimination of the cleaning effort for the dosing means. This is of particular advantage in dosing devices in which the media has to be changed often or which are operated with media that soils the dosing means, and impairs the operability thereof. In known systems great efforts are taken for a frequent cleaning whereas the dosing device of the invention just requires a replacement of the disposable member or members.

Preferably, the piston-cylinder unit is designed as a plastic member whose material is not valuable and which can be recycled in an environment-friendly manner.

For the operation of the dosing means, a particularly preferred embodiment provides for a motor type drive means which drives a coupling means in a longitudinally displaceable manner via a suitable motion converter or gearing. The coupling means, in turn, can be secured to the piston of the piston-cylinder unit so that for the installation of the disposable member the latter need just be inserted into the dosing means and has to be connected with its piston to the drive means via the coupling means.

The dosing unit, in turn, is connected to a valve means which is arranged in the flow path between the withdrawal container and the receiving containers. In a particularly preferred embodiment the valve means comprises a suction valve and a discharge valve which are each preferably designed as check valves arranged in a valve housing or valve head for forming a separable operable and compact uniform component. When the piston of the piston-cylinder unit is moved upwards during operation of the dosing device, a negative pressure is created in the valve head whereupon the suction valve is opened and the medium to be dosed can be sucked in accordingly. In the case of an overpressure, i.e. when the piston of the piston-cylinder unit is pressed downwards, the ejection valve is opened and the dosing operation can be carried out.

Apart from the cylinder-piston units, the valve means, in particular the valve head and the other members of the valve means, may be designed as disposable members, which are in particular made from plastics. The invention is simple in operation because the piston-cylinder units and the valve means can be assembled and disassembled by simple operations rapidly, reliably, in a leak-proof manner and detachably without the need for any tools.

To further improve such an easy operability, the cylinder of the piston-cylinder unit is provided in a particularly preferred embodiment with a threaded connection (in particular a Luer lock connection) and with a sealing cone cooperating with a counter-cone in the valve head. With a corresponding design of the threaded connection, the cylinder can thereby be fixed through half a rotation to the valve head and also tightly connected to the valve head via the two cooperating sealing cones.

The valve head itself can also be tightly mounted on a simple connection pin by being simply attached thereonto. Thus, a special advantage in the inventive dosing device is in particular obtained when the piston-cylinder units and the valve means have to be used as sterilized members. According to the principles in the invention these may be sterilized during production and thus delivered as pre-sterilized members and installed and, after use, they can be easily and efficiently disassembled and disposed of to be replaced by new pre-sterilized members. This offers special advantages insofar as a complicated cleaning process can be dispensed with which would require a previous disassembly of said members and a subsequent sterilization and reinstallation of said old members.

In a further, particularly preferred embodiment, the valve means is arranged on a distributor rail which is in flow communication via a connection line with the withdrawal container. The connection line is preferably designed as a channel which is integrated into the distributor rail and which in a further, particularly preferred embodiment is in flow communication with a bottom member of a compensating container via a connecting bore. The valve means is brought into flow communication with the distributor rail via suitable connection members, such as connection nipples.

The compensating container which is arranged between the withdrawal container and the dosing unit serves to maintain a substantially constant suction pressure; to this end, in a further, particularly preferred embodiment sensors are provided on the compensating container for determining the filling volume. Said sensors can control a pump positioned within the delivery path for the basic delivery of the medium into the compensating container, so that said container has a substantially constant filling volume, which, in turn, ensures a substantially constant input pressure in the valve means.

The provision of the compensating container is advantageous when dosing units of plastics are provided, as their elasticity and inherent conveying inaccuracy can thereby be compensated. In such dosing units only a relatively small suction pressure is allowed to prevail because otherwise the piston-cylinder units would leak and thus become inaccurate as to their delivery rate.

Moreover, a further particularly preferred feature of the compensating container is that it can be provided with a sterile filter if an operation under sterile conditions is required.

Finally, it is possible to support the dosing means such that it is displaceable within the dosing device; to this end the whole dosing means may e.g. be supported to be displaceable along a rail.

A method for operating a dosing device is also provided. In one aspect of the inventive method, a defined drop retraction into the ejection cannula of the dosing means or unit is achieved.

For this purpose, and after dosage, the piston of the piston-cylinder unit is retracted a short defined distance, which relieves the liquid column inside the dosing unit and thus retracts the drop. This is accomplished with the valve body because of its elastic material which will deform upon retraction of the piston of the piston-cylinder unit, thereby permitting a retraction of the liquid column. The one advantage of the invention is that a displaceable dosing unit does not splash any drops which would soil the whole device or system.

Of course the dosing device according to the invention can be adapted to different applications and in many ways. In particular, it is possible to provide a plurality of withdrawal containers and above all a plurality of dosing units of which all are arranged in the dosing means and provided with piston-cylinder units designed as disposable members. Such adaptations are all within the scope of the principles of the present invention.

Further details, features and advantages of the present invention will become apparent from the following description of an embodiment taken in conjunction with the drawings:

DETAILED DESCRIPTION

Figure 1:
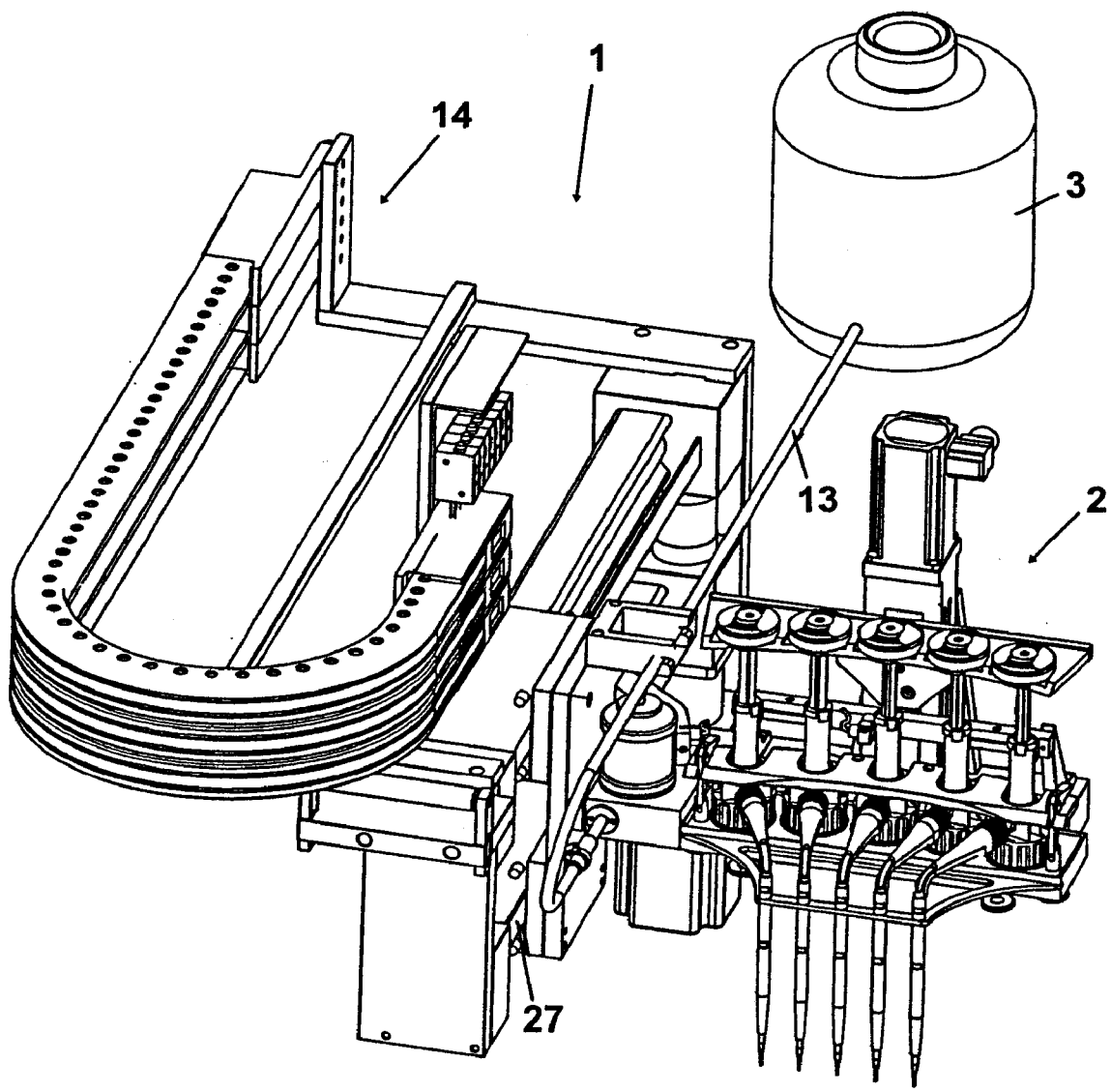
FIG. 1 is a schematically slightly simplified and partial illustration of a dosing device of the invention in a perspective view.

FIG. 1 of the drawing is a schematically slightly simplified perspective and partial view showing a dosing device 1 of the invention which comprises a schematically illustrated withdrawal container 3 and a dosing means designated by reference numeral 2 in its entirety. The dosing means 2 is permanently connected to the withdrawal container 3 via a line connection.

Furthermore, the dosing device 1 according to the invention comprises a system member designated in its entirety by reference numeral 14, which symbolizes all of the electrical means, electrical lines, machine frames, or the like, required for operating the device 1.

Figure 2:
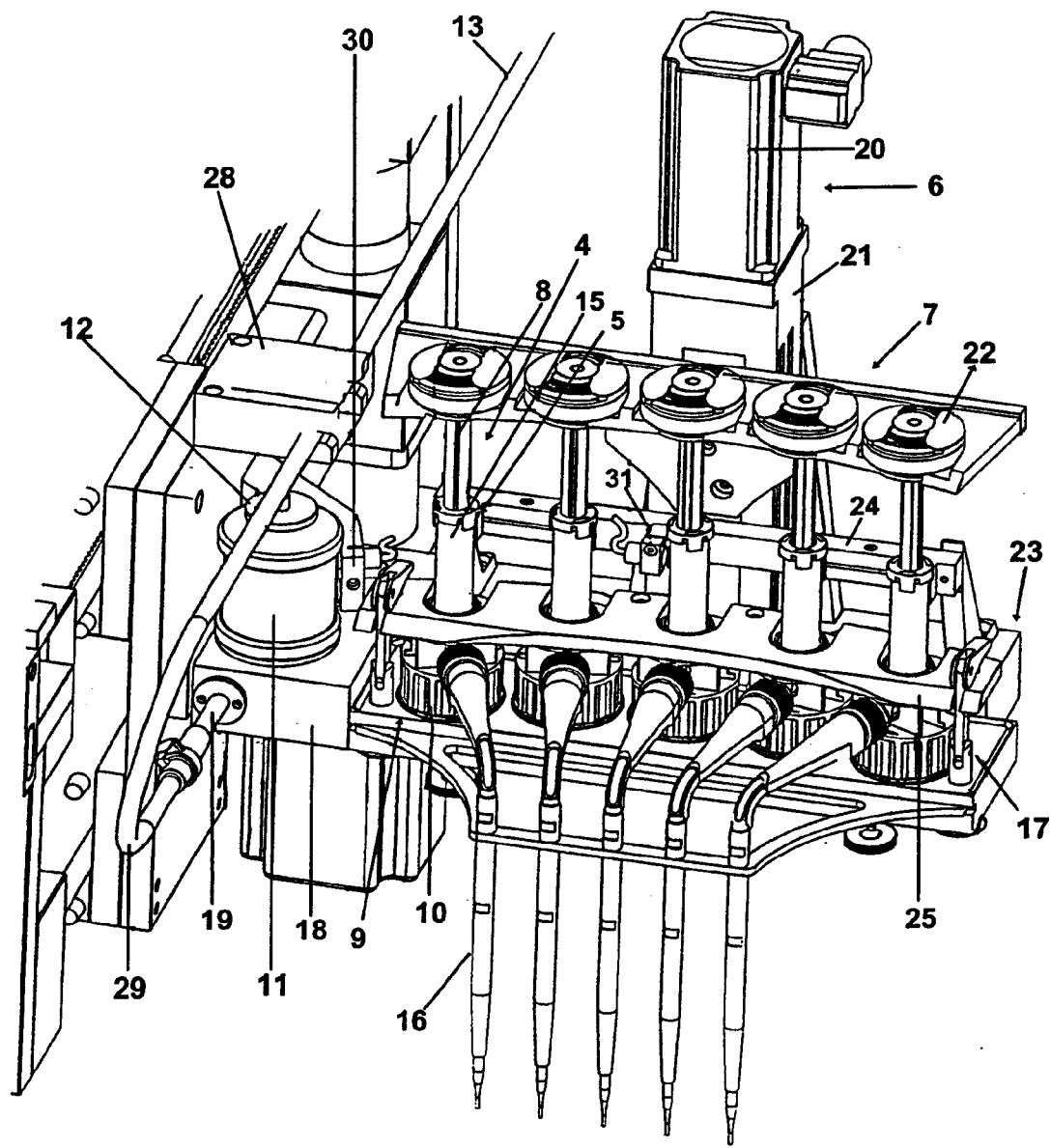
FIG. 2 is an enlarged view according to FIG. 1, showing part of the dosing device according to FIG. 1.

In the example of FIGS. 1 and 2, the dosing means 2 comprises five dosing units, of which one is designated by way of representation with reference numeral 4. Each dosing unit 4, in turn, comprises a piston-cylinder unit 5 which is designed as a disposable member and preferably made from a plastic material and comprises a longitudinally displaceable piston 8 arranged within a cylinder 15. The piston-cylinder unit 5 is arranged on a valve means 9 which comprises a valve housing 10 having arranged therein a suction valve and an ejection valve which, however, are not shown in more detail in the drawing. The ejection valve and the suction valve, however, can be designed in the manner known per se and may comprise a valve body which is movable between an open and a closed position, a valve seat designed accordingly, as well as a seal. The ejection and suction valves may be check valves.

The drawing illustrates that the piston-cylinder unit 5 with its cylinder 15 is mounted on the valve housing 10. Furthermore, an ejection cannula 16 is arranged on the valve housing 10 for discharging the medium to be dosed into receiving containers, which are also not shown in more detail in the drawing.

In the illustrated embodiment the valve housing 10 is mounted on a distributor rail 17. The distributor rail 17 has integrated thereinto a line which is in flow communication with the valve housing 10 via a corresponding connection means, such as connection nipples. Of course, all of the other valve means are connected in this way to the connection line of the distributor rail 17.

The connection line extending in the distributor rail 17 is, in turn, in flow communication with a bottom member 18 of a compensating container 11. The bottom member 18 comprises a connection 19 which can be connected to a line section 29 which is in flow communication with the connection line 13, so that a continuous flow connection is established between the withdrawal container 3 and the valve means 9 and the dosing units 4, respectively. In the illustrated embodiment, the compensating container 11 is provided with a sterile filter 12 and a sensor assembly 30 which controls the filling volume of the compensating container 11 to have an approximately constant value.

Furthermore, the dosing device 1 of the invention comprises a drive means 6 which in the example is designed as a motor type drive means and comprises a motor 20 and a motion converter 21 connected to the motor 20. The motion converter 21 converts the rotary movement of the motor shaft into a longitudinal movement which is transmitted to a coupling means 7 that is in driving connection with the drive means 6. The coupling means 7, in turn, is provided for each piston-cylinder unit 5 with a connection means 22 that is preferably designed as a quick-action clamp and which can detachably be connected to the collar at the free end of the piston 8 of the piston-cylinder unit 5.

The piston-cylinder units 5 and the valve means 9, in turn, are inserted into a holding device 23 which comprises a holding plate 25 arranged above the valve housings 10. Thus, the cylinders of the piston-cylinder units 5 and the valve housings 10 are fixed so that upon a displacement of the coupling means 7 only the pistons 8 in the cylinders 15 are moved up and down to effect the suction stroke and the ejection stroke.

Furthermore, FIG. 2 shows a holding bracket 24 for holding level sensors per piston-cylinder unit 5, of which in FIG. 2 only one sensor 31 is drawn on the holding bracket 24 for simplifying the illustration. The sensors 31 check the filling level for each piston-cylinder unit. In case a wrong filling has been detected, which is e.g. caused by the formation of air bubbles, an error signal is produced via the sensors 31 so that the dosing device according to the invention can either be stopped by a control unit or an automatic de-airing of the piston-cylinder units 5 is carried out. For de-airing purposes it is possible to initiate a rapid upward and downward movement for producing fast stroke movements of the piston 8, which will expel air from the cylinders 15.

For removing air from all cylinders 15 in such a case, it must be ensured that the respective pistons 8 "are moved on block". This means that the pistons 8 have to be moved down to the bottom of the respective cylinder 15. In the particularly preferred embodiment shown in FIG. 2, the quick-action clamps 22 comprise a compensating element, e.g. a spring, in the housing thereof; said spring, however, is not visible in the figure. The compensating element ensures that all of the pistons can be moved on block, if necessary, without damaging the cylinder, the piston or the whole system, as it cannot be guaranteed right from the start due to tolerances in the individual components and mounting tolerances that during the downward movement all of the pistons in each cylinder have an end position aligned with that of the other pistons. Thus, the compensating element makes it possible to move all of the pistons downwards into their lowermost end position for de-airing purposes without any damage being caused thereby.

The whole assembly which comprises the dosing unit 2 and the motor drive means 6 with the above-explained components is supported on the frame of the dosing device 1 to be movable along an axis 27. Furthermore, a tube clip 28 into which the connection line 13, which is normally designed as a flexible tube element, can be inserted is provided on said assembly which is movably supported on the whole. The tube connection member 29 extends from the tube clip 28 to the connector 19.

During operation of the dosing device 1, and depending on the respective application, a corresponding number of dosing units 4, each being designed as a disposable member, are first inserted into the device in the above-described manner so that the piston-cylinder units 5 are arranged on the valve housings 10 and the pistons 8 are connected to the coupling means 7. During operation the coupling means 7 is moved up and down with the help of the drive means 6, which effects a reciprocating movement of the pistons 8 in the cylinders 15, so that the suction stroke and the ejection stroke can be carried out. The medium is here withdrawn from the withdrawal container 3 via the opening and closing suction valves and ejection valves of the valve means 9. The sensor assembly 30 on the compensating container 11 guarantees that a substantially constant filling volume is present in the compensating container 11, which effects a constant suction pressure in the connection line and thus a constant suction pressure for the piston-cylinder units 5, said pressure being preferably set to a small value so that the piston-cylinder units 5, which are normally made from plastics, are tight, thus exhibiting a high delivery accuracy.

What is claimed is:

1. A dosing device comprising
   at least one withdrawal container; and
   dosing means which is in line communication with the withdrawal container and which discharges the medium to be dosed to receiving containers;
   said dosing means comprises at least one dosing unit which is a piston-cylinder unit, and that said at least one dosing unit is in flow communication with a valve means; and
   said dosing means includes said valve means said valve means being in flow communication with the withdrawal container and receiving containers, said valve means comprising a suction valve and an ejection valve, said suction and ejection valves being formed as non-return valves.

2. The dosing device according to claim 1, characterized in that said piston-cylinder unit is made from plastic.

3. The dosing device according to claim 1, characterized in that said dosing means comprises a motor drive means which is connected to a longitudinally displaceable coupling means that can be secured to the piston of said dosing unit.

4. The dosing device according to claim 3, characterized in that said coupling means comprises a quick-action clamp which is provided with a compensating element.

5. The dosing device according to claim 1, characterized in that said valve means is made of plastic.

6. The dosing device according to claim 1 or 5, wherein the suction valve and the ejection valve are arranged within a valve housing.

7. The dosing device according to any one of claims 1 to 5, characterized in that said valve means is arranged on a distributor rail which is in flow communication via a connection line with said withdrawal container.

8. The dosing device according to any one of claims 1 to 5, characterized in that a compensating container is arranged between said withdrawal container and said dosing unit for maintaining a substantially constant negative suction pressure in said connection line.

9. The dosing device according to claim 8, characterized in that said compensating container is provided with a sterile filter.

10. The dosing device according to claim 8, wherein said compensating container is provided with a sensor assembly for controlling a pump in said connection line leading to said withdrawal container, so that the filling volume of said compensating container is approximately constant.

11. The dosing device according to any one of claims 1 to 5, characterized in that said dosing means is supported in a displaceable manner.

12. The dosing device according to claim 6 characterized in that said valve means is arranged on a distributor rail which is in flow communication via a connection line with said withdrawal container.

13. The dosing device according to claim 6 characterized in that a compensating container is arranged between said withdrawal container and said dosing unit for maintaining a substantially constant negative suction pressure in said connection line.

14. The dosing device according to claim 7 characterized in that a compensating container is arranged between said withdrawal container and said dosing unit for maintaining a substantially constant negative suction pressure in said connection line.

15. The dosing device according to claim 9 wherein said compensating container is provided with a sensor assembly for controlling a pump in said connection line leading to said withdrawal container so that the filling volume of said compensating container is approximately constant.

16. The dosing device according to claim 6 characterized in that said dosing means is supported in a displaceable manner.

17. The dosing device according to claim 7 characterized in that said dosing means is supported in a displaceable manner.

18. The dosing device according to claim 8 characterized in that said dosing means is supported in a displaceable manner.

19. The dosing device according to claim 9 characterized in that said dosing means is supported in a displaceable manner.

20. The dosing device according to claim 10 characterized in that said dosing means is supported in a displaceable manner.

21. A method for operating a dosing device comprising at least one withdrawal container and a dosing means which is in line communication with said withdrawal container and which discharges medium to be dosed to receiving containers, said method including:

inserting a piston-cylinder unit and a valve means into a dosing means wherein the piston-cylinder unit is connected to a drive means;

operating the dosing means through a dosing cycle;

removing the piston-cylinder unit and valve means after the dosing cycle;

disposing of the thus removed piston-cylinder unit and valve means; and replacing the thus removed piston-cylinder unit and valve means with an unused piston-cylinder unit and an unused valve means.

22. The method according to claim 21, including retracting said medium into an ejection cannula by retracting a piston in a cylinder of said piston-cylinder unit a defined distance for pressure relief of the liquid column after dosing so that a drop of medium at the tip of the cannula is retracted.

* * * * *

UNITED STATES PATENT AND TRADEMARK OFFICE
CERTIFICATE OF CORRECTION

PATENT NO. : 6,593,146 B1
DATED : July 15, 2003
INVENTOR(S) : Andreas Lang et al.

It is certified that error appears in the above-identified patent and that said Letters Patent is hereby corrected as shown below:

Column 1,
Line 48, delete "a frequent";

Column 2,
Lines 39-40, delete "dispensed with" and replace with -- disposed of --;

Column 5,
Line 56, after the word "discharges" delete "the" and replace with -- a --;
Line 59, after the word "and" delete "that";
Lien 67, delete "non-return" and replace with -- check --;

Column 7,
Line 8, after the phrase "drive means" insert -- and said valve means comprises a suction valve and ejection valve, said suction and ejection valves being formed as check valves --.

Signed and Sealed this

Fourth Day of November, 2003

JAMES E. ROGAN
*Director of the United States Patent and Trademark Office*